United States Patent
Nakatsuka

(10) Patent No.: US 6,640,635 B2
(45) Date of Patent: Nov. 4, 2003

(54) METHOD OF MEASURING HYDROGEN CONCENTRATION OF RADIOACTIVE METALLIC MATERIAL

(75) Inventor: Masafumi Nakatsuka, Ibaraki-Ken (JP)

(73) Assignees: Kabushiki Kaisha Toshiba, Tokyo (JP); Hitachi Ltd., Tokyo-To (JP); Nippon Nuclear Fuel Development Co., Ltd., Higashi-Ibaraki-gun (JP)

( * ) Notice: Subject to any disclaimer, the term of this patent is extended or adjusted under 35 U.S.C. 154(b) by 35 days.

(21) Appl. No.: 10/011,486

(22) Filed: Dec. 11, 2001

(65) Prior Publication Data

US 2002/0069703 A1 Jun. 13, 2002

(30) Foreign Application Priority Data

Dec. 11, 2000 (JP) ......................................... 2000-375957

(51) Int. Cl.[7] .......................... G01N 29/12; G01N 29/24
(52) U.S. Cl. ............................ 73/643; 73/602; 73/622; 73/579
(58) Field of Search ........................ 73/602, 622, 623, 73/643, 579; 376/249, 250, 252

(56) References Cited

U.S. PATENT DOCUMENTS

| 4,305,294 A | * | 12/1981 | Vasile et al. | ........... | 73/579 |
| 4,685,334 A | | 8/1987 | Latimer | ................. | 73/599 |
| 5,811,682 A | * | 9/1998 | Ohtani et al. | ............. | 73/643 |
| 5,895,856 A | * | 4/1999 | Johnson et al. | ............ | 73/643 |
| 6,109,108 A | | 8/2000 | Ohtani et al. | ............. | 73/599 |

FOREIGN PATENT DOCUMENTS

| DE | 34 04 232 | 8/1985 |
| DE | 196 24 512 | 1/1998 |
| DE | 19700954 A1 | * 7/1998 | ......... G01N/29/12 |
| JP | 62-179660 | 8/1987 |
| JP | 1-163653 | 6/1989 |
| JP | 9-257760 | 10/1997 |

OTHER PUBLICATIONS

Moles et al., "Ultrasonic Measurement of Hidride Platelet Concentration in Zirconium Pressure Tubes", Nondestructive Evaluation: NDE Planning and Application: Presented at the 1989 ASME Pressure Vessels and Piping Conference—JSME Co–Sponsorship, Jul. 23–27, 1989, vol. 5, pp. 205–211.

Hutchins et al., "Temperature–dependent NDE of Hydrided Zr–Nb Tubing", Insight–Non–Destructive Testing and Condition Monitoring, Feb. 1996, vol. 38, No. 2, pp. 102–107.

Billson et al., "Ultrasonic Evaluation of Hydride Concentration in Zirconium–Niobium Alloys", Ultrasonics, IPC Science and Technology Press Ltd., vol. 35, No. 3, May 1, 1997, pp. 241–249.

(List continued on next page.)

Primary Examiner—Helen Kwok
Assistant Examiner—Rose M. Miller
(74) Attorney, Agent, or Firm—Foley & Lardner

(57) ABSTRACT

Electromagnetic acoustic resonance method by using EMAT is used for determining hydrogen concentration of radioactive metallic object. In one preferred embodiment, resonance frequencies fr, fr are measured with the EMAT, where where fr is a resonance frequency when a direction of an amplitude of a transverse ultrasonic wave generated by the EMAT is the same as the rolling direction of the metallic object of rolled material, and ft is a resonance frequency when a direction of the amplitude of the transverse ultrasonic wave is perpendicular to the rolling direction. A value R is calculated by using: $R=(fr-ft)/\{(fr+ft)/2\}$. The hydrogen concentration of the metallic object is calculated on the basis of the experimentally determined relation between the value R and hydrogen concentration.

6 Claims, 3 Drawing Sheets

OTHER PUBLICATIONS

Hirao et al., "Electromagnetic Acoustic Resonance and Materials Characterization", Ultrasonics, IPC Science and Technology Press Ltd., vol. 35, No. 6, Sep. 1, 1997, pp. 413–421.

Ogi et al, "Contactless Mode–Selective Resonance Ultrasound Spectroscopy: Electromagnetic Acoustic Resonance", Journal of the Acoustical Society of America, American Institute of Physics, vol. 106, No. 2, Aug. 1999, pp. 660–665.

Tanaka et al., "Evaluation of Elastic Strain Energy Associated with the Formation of Hydride Precipitates in $LaNi_5$", Intermetallics, Elsevier Science Publishers B.V., vol. 8, No. 5–6, May 2000, pp. 613–618.

"Complete Computer Controlled Systems", RITEC Inc., Mar. 8, 2002.

Saneyoshi et al., "Cho–Ompa Gijutu Binran," The Nikkan Kogyo Shimbun Litd. (1978), pp. 90–112, 1669–1683.

Mori et al., "Eddy–Current Test III," the Journal of The Japanese Society for Non–Destructive Inspection (1990), pp. 1–4.

Ogi et al., "Hihakai Kensa," The Journal of The Japanese Society for Non–Destructive Inspection, vol. 43, No. 12 (1994), pp. 764–770.

* cited by examiner

METHOD OF MEASURING HYDROGEN CONCENTRATION OF RADIOACTIVE METALLIC MATERIAL

BACKGROUND OF THE INVENTION

1. Field of the Invention

The present invention relates to a method of non-destructively measuring the hydrogen concentration of a radioactive metallic material by using an electromagnetic acoustic resonance.

2. Description of the Related Art

Metallic materials are likely to be brittle due to high hydrogen concentration thereof. Thus, metallic materials in use in a nuclear power plant are tested for hydrogen absorption.

There are various hydrogen-measuring methods of measuring a very small quantity of hydrogen contained in a metallic material. One of those known hydrogen-measuring methods is a fusing method, which has the following steps. Less than 1 grams of specimen is sampled from an object of measurement. The specimen is fragmented, rinsed and dried, and the weight of the specimen is measured. Then, the specimen and a pure metal serving as a fusing agent are put in a refractory crucible, the specimen is melted at a temperature lower than the melting point of the specimen in an inert gas atmosphere to extract hydrogen together with other gases from the specimen. The extracted gas is collected in a container of a fixed volume including a thermal conductivity cell and the thermal conductivity of the gas is measured. The quantity of hydrogen contained in the gas is determined on the basis of the measured thermal conductivity of the gas, and the hydrogen concentration of the specimen is calculated on the basis of the quantity of hydrogen. Although this hydrogen measuring method is capable of determining hydrogen concentration in a high accuracy on the order of several tens parts per million, the hydrogen measuring method requires skilled work to sample the specimen from the measuring object and to fragment the specimen.

Another hydrogen measuring method cuts out a small, beam-shaped test piece from a measuring object and estimates the hydrogen concentration of the test piece by using the vibration attenuation characteristic of the test piece called internal friction featured by a hydride contained in the test piece.

The application of the foregoing destructive test method to testing a radioactive object made of metallic material is subject to many restrictions. The destructive test method must be carried out in an installation provided with various facilities meeting legal requirements on shields for analyzers, exhaust systems and such to ensure the perfect protection of operators participating in the test from exposure to radioactive rays and the perfect prevention of environmental radioactive contamination. The construction, maintenance and management of such an installation for analysis need very high costs.

An object to be inspected removed from a nuclear power plant must be transported to an installation for analysis by the following procedure, which requires much time and labor and high costs. An assembly including the object to be inspected is immersed in water in a pool annexed to a nuclear reactor to protect operators from exposure to radiation, and the object is removed from the assembly by means of a remote-controlled system. The object is put into an approved container called a cask proved to be capable of shielding radiation by a remote-controlled system. The cask containing the object is transported to an inspection installation under conditions meeting rules and provisions specified by relevant laws after obtaining permissions from government offices concerned and all the local governments on the route of transportation of the cask.

As mentioned above, the known test methods require much time and labor and high costs because the known test methods are of a destructive test system. The inventors of the present invention examined various non-destructive test methods that can be carried out in a pool annexed to a nuclear reactor.

An eddy-current test method is one of the nondestructive test methods examined. The eddy-current test method is applied widely to various tests including tests for determining a heat-treatment condition, measuring internal stress and evaluating structures. The eddy-current test method is mentioned in, for example, "Eddy-current Test III", MORI et al, The Japanese society for Non-Destructive Inspection (JSNDI), (1990). The eddy-current test method is applied not only to the detection of defects in objects, but also to various industrial purposes including the determination the quality of objects, the measurement of the thickness of films, measurement of dimensions of objects and the measurement of displacement. The electromagnetic characteristic, such as electric conductivity or magnetic permeability, of a metallic material changes slightly, depending on the hydride content of the metallic material. Therefore, the application of the eddy-current test method to the measurement of hydrogen concentration is theoretically feasible. However, the eddy-current test method is not sufficiently sensitive to the variation of hydrogen concentration, and is subject to many factors of noise generation, such as distance between the test coil and the specimen, irregularities in the surface of the specimen, electromagnetic properties of the specimen, measurement environment and measuring speed, and hence is not suitable for hydrogen concentration measurement.

Another known method examined is an ultrasonic test method, which measures the velocity and attenuation characteristic of a sound wave propagating through a metallic material with an ultrasonic probe, and determines the quantity of hydrogen contained in the metallic material on the basis of measured data. It is generally known as mentioned in, for example, "Cho-Ompa Gijutu Binran", SANEYOSHI et al, The Nikkan Kogyo Shimbun Ltd., (1978), that the velocity and attenuation characteristic of an ultrasonic wave propagating through the metallic material is dependent on features of the metallic material, such as crystal grain size, hardness and crystalline dislocation. However, since the ultrasonic test method uses the contact-type ultrasonic probe, a large amount of vibrational energy is absorbed by a coupling medium lying between the ultrasonic probe and the metallic material, and hence the accurate detection of a change in the vibrational energy absorbing characteristic of the metallic material due to the formation of a hydride in the metallic material cannot practically be achieved. Thus, the application of the ultrasonic test method to the measurement of the hydrogen concentration of a metallic object is infeasible.

An electromagnetic acoustic resonance method that uses an electromagnetic acoustic transducer (hereinafter, abbreviated to "EMAT") for the detection of the interior condition of an object has been recently developed. Techniques relating to this method are known and mentioned in, for example, "Hihakai Kensa (Journal of JSNDI)", The Japanese Society for Non-Destructive Inspection (JSNDI), Vol. 43, No. 12 (December, 1994). However, the application of the techniques to the nondestructive test for the determination of the hydrogen concentration of a metallic object has not been known.

SUMMARY OF THE INVENTION

The object of the present invention is to provide a method of non-destructively measuring a concentration of hydrogen contained in a radioactive test object of metallic material by using the electromagnetic acoustic resonance method.

According to the present invention, there is provided a method of measuring a concentration of hydrogen contained in a radioactive test object of metallic material. The method including the steps of: positioning an EMAT adjacent to the object, the EMAT including a magnet that creates a static magnetic field and a coil that creates a magnetic field variable with time; supplying a radio-frequency current to the coil of the EMAT, thereby generating an ultrasonic wave that is reflected for multiple reflection by opposite surfaces of the object; changing a frequency of the radio-frequency current, thereby finding a resonance frequency that make the object exhibit electromagnetic acoustic resonance by means of a detector connected to the coil of the EMAT; and determining the concentration of hydrogen contained in the object on the basis of an experimentally determined relation between the numerical value and the hydrogen concentration of the object, the numerical value being calculated by using an expression including the resonance frequency as a valuable.

According to the present invention, the hydrogen concentration of the test object can be readily determined nondestructively, upon highly accurately grasping the elastic-vibration characteristic, which is most sensitive to the variation of the hydrogen concentration of the metallic material.

BRIEF DESCRIPTION OF THE DRAWINGS

The above and other objects features and advantages of the present invention will become more apparent form the following description taken in connection with the accompanying drawings, in which.

DESCRIPTION OF THE PREFERRED EMBODIMENTS

Figure 1:
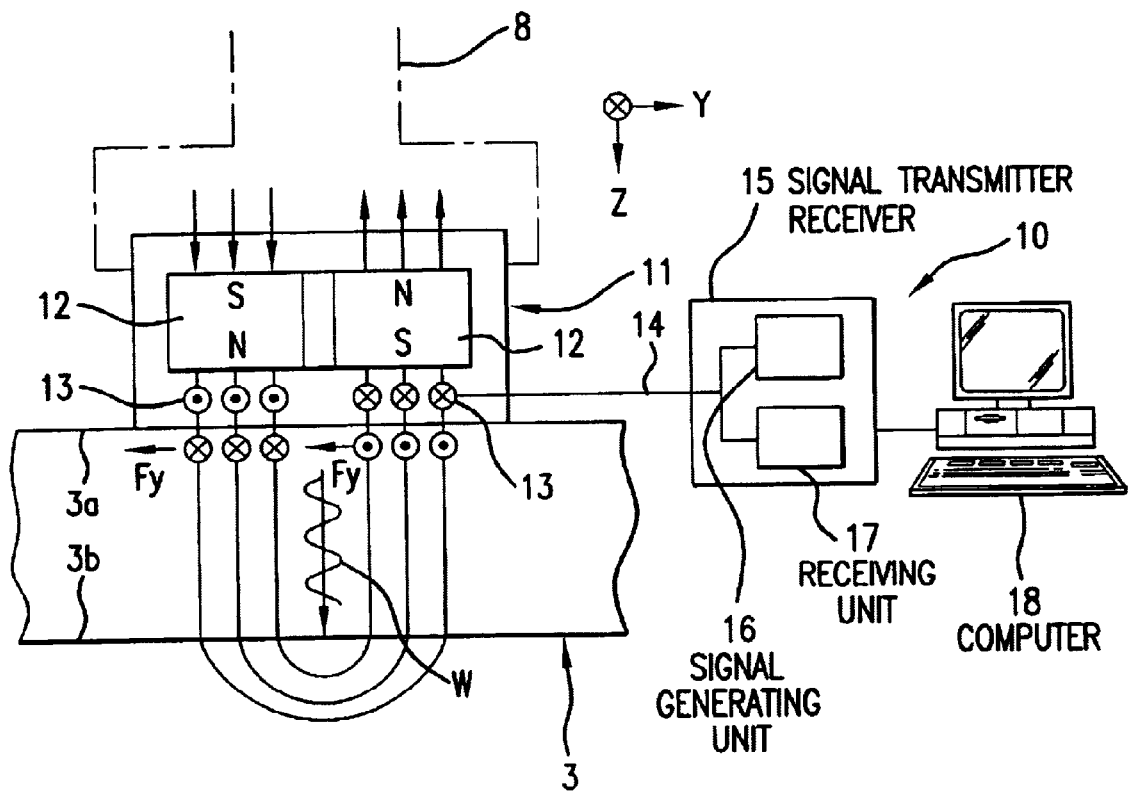
FIG. 1 is a diagrammatic view of assistance in explaining a hydrogen concentration measuring system for carrying out a hydrogen concentration measuring method in a preferred embodiment according to the present invention.

Referring to FIG. 1, a hydrogen concentration measuring system 10 includes an EMAT 11. The EMAT 11 has a permanent magnet 12 and a coil 13. The permanent magnet 12 creates a static magnetic field in the vicinity of a surface $3a$ of a test object 3 made of metallic material (hereinafter referred to as "metallic object"). The coil 13 creates an oscillatory magnetic field, i.e., a magnetic field of an intensity variable with time. The permanent magnet 12 may be substituted by an electromagnet that creates a static magnetic field.

The coil 13 of the EMAT 11 is connected to a signal transmitter-receiver 15 by a signal cable 14. The signal transmitter-receiver 15 has a variable-frequency signal-generating unit 16. The signal generating unit 16 generates a sinusoidal burst wave of a frequency in the range of several kilohertzs to several tens megahertzs, and is capable of continuously varying the frequency of the burst wave.

When high-frequency current, such as a radio-frequency current, is supplied to the coil 13 of the EMAT 11 by the signal transmitter-receiver 15, a magnetic field of an intensity varying with time is created in the vicinity of the surface $3a$ of the metallic object 3, and an eddy current is induced in the vicinity of the surface $3a$ of the metallic object 3. The eddy current tends to counteract the change of the magnetic field and flows in a direction to opposite to that of the current flowing through the coil 13 is produced. The eddy current and the static magnetic field created by the permanent magnet 12 interact to generate a Lorentz force Fy. The Lorentz force Fy acts on free electrons in the metallic object. Then, the free electrons collide against the crystals of the metallic object to cause the crystals to move and, consequently, the crystals generate an ultrasonic wave. The z-direction component of the static magnetic field created in the vicinity of the metallic object by the EMAT 11 shown in FIG. 1 is large, the Lorentz force Fy act mainly in a y-direction. Consequently, an ultrasonic transverse wave W, in which each point of the medium is disturbed in the y-direction, i.e., in horizontal directions as viewed in FIG. 1, is generated.

The ultrasonic transverse wave W propagates in the z-direction parallel to the thickness of the metallic object 3, and is reflected by the other surface $3b$, opposed to the surface $3a$, of the metallic object 3 toward the surface $3a$ of the same. The reflected ultrasonic transverse wave W disturbs the static magnetic field created by the permanent magnet 12, and an electromagnetic field tending to counterbalance the disturbance of the static magnetic field is created in the vicinity of the metallic object 3. The ultrasonic transverse wave W attenuates as the same is reflected repeatedly by the surfaces $3a$ and $3b$ for multiple reflection. Therefore, when the frequency of the radio-frequency current supplied to the coil 13 is varied, the reflected waves resonate at a specific frequency. This phenomenon is called "electromagnetic acoustic resonance".

The transmitter-receiver 15 has a receiving unit 17 to detect the variation of the intensity of the magnetic field through the coil 13. Preferably, the receiving unit 17 is a superheterodyen receiver. The receiving unit 17 includes an analog integrator that integrates the product of the amplitude and phase of a detection signal with respect to time.

Figure 2:
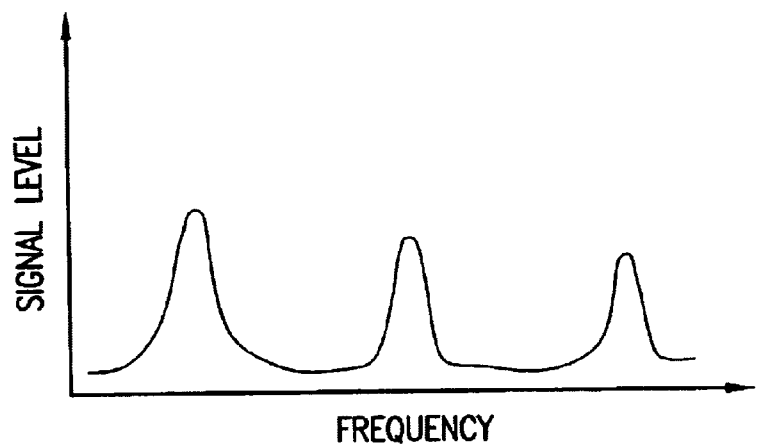
FIG. 2 is a graph showing a resonance spectrum by way of example.

A computer 18 included in the hydrogen concentration measuring system 10 processes the output of the analog integrator of the receiving unit 17 in connection with frequency to provide data representing a resonance spectrum as shown in FIG. 2. Peaks in the resonance spectrum shown in FIG. 2 correspond to electromagnetic acoustic resonance.

An electromagnetic acoustic resonance method itself is well-known and is published in "Hihakai Kensa (Journal of JSNDI)", The Japanese Society for Non-Destructive Inspection (JSNDI), Vol. 43, No. 12 (December, 1994) mentioned in connection with the description of the background art, and hence the further description thereof will be omitted. "RITEC RAM-10000" commercially available from RITEC Inc., Warwick, R.I., USA, can be used for the hydrogen concentration measuring system 10, notably for the transmitter-receiver 15.

The gist of the present invention is to determine the hydrogen concentration of the metallic object by a nondestructive method on the basis of a special relation, which was found by the inventor of the present invention, between resonance frequency detected by the electromagnetic acoustic resonance method and the hydrogen concentration of the metallic object. The hydrogen concentration measuring method in a preferred embodiment according to the present invention will be described hereinafter.

Figure 3:
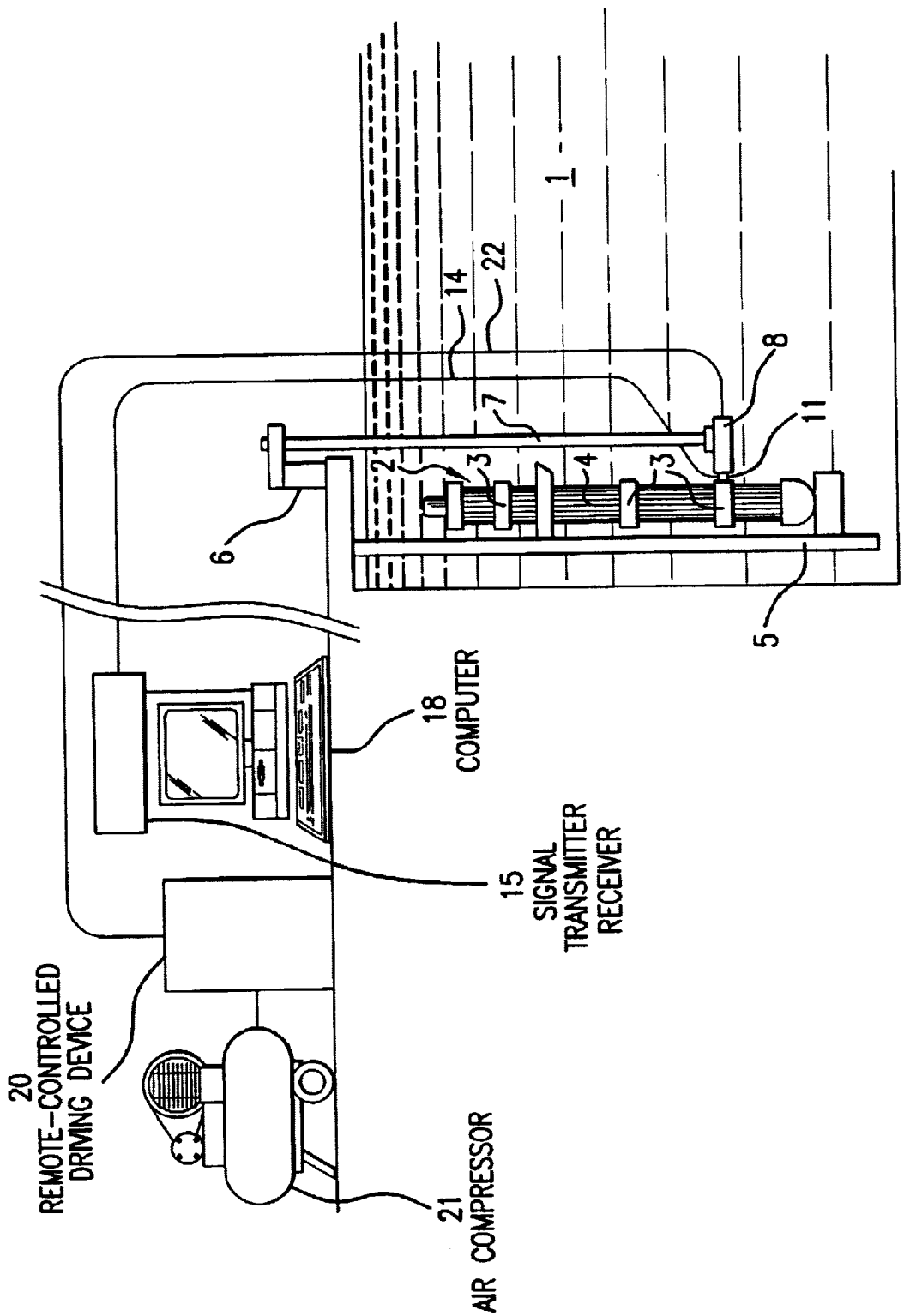
FIG. 3 is a pictorial view of assistance in explaining operations for measuring the hydrogen concentration of a band of a spacer for spacing fuel rods with the help of the hydrogen concentration measuring method of the present invention.

FIG. 3 is a pictorial view of assistance in explaining operations for measuring the hydrogen concentration of a band 3 (i.e., a metallic object), which is a part of a spacer of a fuel assembly 2, by the hydrogen concentration measuring method of the present invention. The spacer spaces fuel cladding tubes 4. The band 3 is a metal plate for bundling a plurality of cylindrical members forming the spacer. As generally known by the skilled in the art, the spacer and the band 3 is formed of a zirconium alloy which hardly absorbs neutrons. A thin zirconium alloy plate forming a channel box can be a measuring object.

The fuel assembly 2 is removed from a nuclear reactor, and is moved into water filled in a pool 1 annexed to the nuclear reactor by a remote-controlled crane, not shown. Then, the fuel assembly 2 is held in an upright position by a holding device 5 in water filled in the pool 1. A pole 7 is held in the pool 1 by a holding device 6, which can move the pole 7 vertically. A pneumatically-driven positioning device 8 is held on the lower end of the pole 7. The positioning device 8 holds and locates the EMAT 11 relative to the band 3.

The components of the hydrogen concentration measuring system 10 including the transmitter-receiver 15, the computer and such and excluding the EMAT 11 are positioned apart from the pool 1 for the security of the operators. The transmitter-receiver 15 and the EMAT 11 are connected by the signal cable 14 extended to a working position. The positioning device 8 is controlled by a remote-controlled driving device 20 disposed at the working position for the security of the operators. The remote-controlled driving device 20 supplies compressed air provided by an air compressor 21 through an air hose 22 to the positioning device 8 to drive the positioning device 8 for positioning the EMAT 11 relative to the band 3. The permanent magnet 12 and the coil 13 are combined in a module and the module is sealed in a resin to protect the permanent magnet 12 and the coil from water and to locate the permanent magnet 12 and the coil 13 of the EMAT 11 properly.

The special relation between resonance frequency and the hydrogen concentration of the metallic object found by the inventors of the present invention will be described. As generally known, the spacer and the band 3 are formed of rolled zirconium alloy materials. The zirconium alloys have crystal structure of the hexagonal system and an orthotropic elastic property.

It was found through the inventor's studies that, in the zirconium alloy plate, there is a highly linear relation between value R expressed by:

$$R = (ft-fr)/\{(ft+fr)/2\} \qquad (1)$$

and the hydrogen concentration of the zirconium alloy plate. In Expression (1), fr is a resonance frequency when the direction of the amplitude of a transverse ultrasonic wave generated by the EMAT 11 is the same as the rolling direction of the rolled zirconium alloy material, and ft is a resonance frequency when the direction of the amplitude of a transverse ultrasonic wave generated by the EMAT 11 is perpendicular to the rolling direction of the rolled zirconium alloy material.

Figure 4:
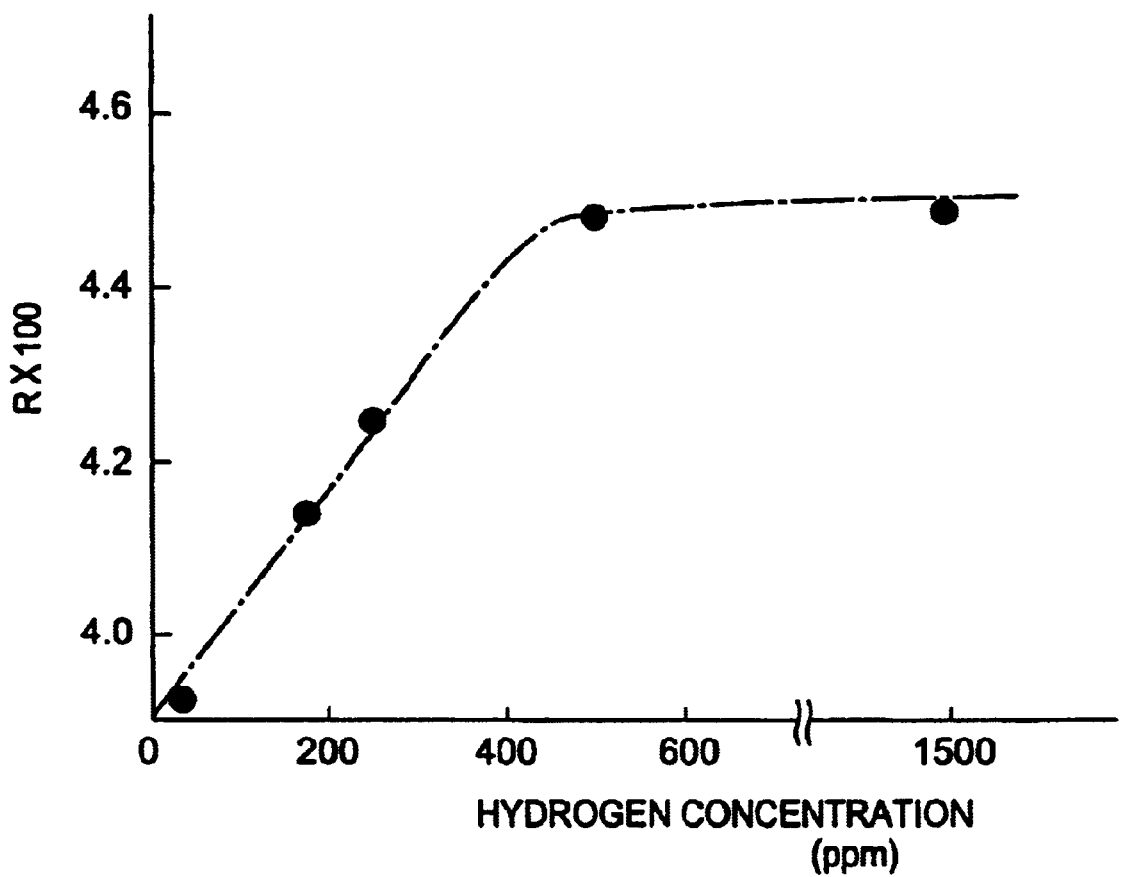
FIG. 4 is a graph showing the relation between a value dependent on resonance frequency, and hydrogen concentration.

The graph shown in FIG. 4 indicates the relation between hydrogen concentration and the value R. Samples of zirconium alloy plates containing hydrogen were prepared to obtain data for the graph of FIG. 4. The samples were subjected to measurement by electromagnetic acoustic resonance method, in water, in order to determine values R of the samples. Thereafter, the samples were subjected to destructive measurement to determine hydrogen concentration. The destructive measurement was carried out by using "LECO Hydrogen Determinator" commercially available from LECO Corporation, St. Joseph, Mich., USA.

In the graph shown in FIG. 4, the abscissa axis represents hydrogen concentration (ppm), and the ordinate axis represents the value R×100 (%). When the hydrogen concentration is 0 ppm, ft is greater than fr by about 4% and R is about 0.04. The value R changes substantially linearly with the change of the hydrogen concentration in the range of 0 to 500 ppm.

The computer 18 of the hydrogen concentration measuring system 10 for carrying out the hydrogen concentration measuring method of the present invention stores a program specifying a procedure for calculating hydrogen concentration on the basis of fr and ft, and database including data represented by the graph shown in FIG. 4.

The steps of the hydrogen concentration measuring method will be described with reference to FIGS. 1 and 3.

First, the EMAT 11 is disposed near the band 3, i.e., the metallic object, in a position such that the direction of the amplitude of the ultrasonic transverse wave induced in the rolled material of the band 3 by the EMAT 11 coincides with the rolling direction (the y-direction, in FIG. 1) of the band 3. It is a technical common sense that, when making a mechanical member of a rolled material, the rolled material is processed such that the rolling direction has a longer dimension. Thus, the rolling direction of the band 3 is known.

In view of achieving accurate measurement, it is desirable that the coil 13 of the EMAT 11 is electrically isolated from the band 3 and is positioned as close to the band 3 as possible. Since the permanent magnet 12 and the coil 13 of the EMAT 11 are combined in a module and the module is sealed in a resin, the EMAT module can be put in close contact with the band 3.

After thus disposing the EMAT 11, the frequency of the radio-frequency current supplied to the coil 13 of the EMAT 11 by the signal transmitter-receiver 15 is varied continuously to find the resonance frequency fr at which the band 3 exhibits electromagnetic acoustic resonance.

Subsequently, the positioning device 8 turns the EMAT 11 through 90° so that the direction of the amplitude of the transverse wave is perpendicular to the rolling direction of the rolled material forming the band 3. After thus disposing the EMAT 11, frequency of the radio-frequency current supplied to the coil 13 of the EMAT 11 by the signal transmitter-receiver 15 is varied continuously to find the resonance frequency ft at which the band 3 exhibits electromagnetic acoustic resonance. The resonance frequencies fr and ft of the same order are used. Test measurement showed that measurement can be achieved in the highest accuracy when third-order resonance frequencies are used.

Measurement based on the value R expressed by Expression (1) is accompanied by the following advantages. The resonance frequencies fr and ft and the frequency difference (ft−fr) are dependent on the thickness of the metallic object, and hence those values for different metallic objects are different. The effect of the thickness of the metallic object on the measurement can be eliminated by dividing the frequency difference (ft−fr) by the mean frequency (ft+fr)/2.

Since the division of the frequency difference by the sum of the frequencies is the essence of Expression (1), "R=(ft−fr)/(ft+fr)", "R=1−fr/(ft+fr)" or "R=fr/(ft+ft)" may be used instead of Expression (1).

The aforementioned measuring method can be used when the object is made of metallic material having crystal structure of the hexagonal system and an orthotropic elastic property, such as zirconium alloys and titanium alloys.

It is possible that the resonance frequencies are affected by the thickness of an oxide film coating the surface of the metallic object. Therefore, it is preferable in view of improving measuring accuracy that the database stored in the computer 18 includes data representing the relation between hydrogen concentration and resonance frequency for oxide films of different thicknesses.

The thickness of the oxide film coating the surface of the metallic object can be readily determined by a known nondestructive test method, such as an eddy-current test method, which itself is a well-known art. More specifically, an eddy-current test method disposes a coil (not shown) for inducing an eddy current in the surface of a measuring object near the measuring object 3, and supplies a radio-frequency current to the coil to induce an eddy current in the measuring object 3. When the oxide film coating the surface of the measuring object 3 disturbs the eddy current, magnetic flux induced by the eddy current varies and an electromotive force is generated in the coil by self-induction. The electromotive force is observed to determine the thickness of the oxide film, i.e., nonconductive layer, coating the surface of the measuring object. The thickness of the oxide film or the like coating the surface of the measuring object is measured prior to the measurement of the hydrogen concentration by the electromagnetic acoustic resonance method and data on the thickness of the oxide film is stored in the computer 18. The computer 18 calculates a hydrogen concentration properly, using the data previously stored therein.

The frequencies fr (or ft) of different orders may be compared instead of using the value R calculated by using Expression (1). For example, the ratio of the resonance frequency ft of the third order to the resonance frequency ft of the first order is not exactly 3.0 and is dependent on hydrogen concentration. Thus, a numerical value R' expressed by: $R'=(fn/fm)/(n/m)$ where fn is a resonance frequency of n-th order, fm is a resonance frequency of m-th order, and n and m are orders of resonance may be used instead of aforementioned R.

Such a hydrogen concentration measuring method also has an advantage that the use of the ratio of the resonance frequency of a higher order to that of a lower order for determining hydrogen concentration eliminates the effect of the thickness of the measuring object on the measurement of hydrogen concentration. However, more precise measurement is possible upon using the aforementioned numerical value R rather than using the numerical value R'.

The measurement by using electromagnetic resonance method is carried out with the object and the EMAT being submerged in water in the aforementioned embodiments, however, the measurement can be carried out in the air.

What is claimed is:

1. A method of measuring a concentration of hydrogen contained in a radioactive test object of metallic material, said method comprising the steps of:

positioning an electromagnetic acoustic transducer (EMAT) adjacent to the object, the EMAT including a magnet that creates a static magnetic field and a coil that creates a magnetic field variable with time;

supplying a radio-frequency current to the coil of the EMAT, thereby generating an ultrasonic wave that is reflected for multiple reflections by opposite surfaces of the object;

changing a frequency of the radio-frequency current, thereby finding a resonance frequency that makes the object exhibit electromagnetic acoustic resonance by means of a detector connected to the coil of the EMAT; and determining the concentration of hydrogen contained in the object on the basis of an experimentally determined relation between a numerical value and the hydrogen concentration of the object, the numerical value being calculated by using an expression including the resonance frequency as a variable, wherein the object is formed from a rolled material, and the numerical value is calculated by dividing a difference between ft and fr by a sum of ft and fr or an average of ft and fr, where fr is a resonance frequency when a direction of an amplitude of a transverse ultrasonic wave generated by the EMAT is the same as the rolling direction of the rolled material, and ft is a resonance frequency when a direction of an amplitude of a transverse ultrasonic wave generated by the EMAT is perpendicular to the rolling direction of the rolled material.

2. The method according to claim 1 further comprising the step of measuring a thickness of an oxide film coating a surface of the object, wherein the relation used in the step of determining the concentration of hydrogen is experimentally determined for the thickness of the oxide film.

3. The method according to claim 1, wherein the object is a member of a nuclear reactor or a member of a fuel assembly charged in the nuclear reactor, said method further comprising the steps of:
 removing the object from the nuclear reactor;
 submerging the object in water filled in a pool annexed to the nuclear reactor;
 wherein the EMAT is disposed adjacent to the object and submerged in the water in the step of positioning the EMAT.

4. A method of measuring a concentration of hydrogen contained in a radioactive test object of metallic material, said method comprising the steps of:

positioning an electromagnetic acoustic transducer (EMAT) adjacent to the object, the EMAT including a magnet that creates a static magnetic field and a coil that creates a magnetic field variable with time;

supplying a radio-frequency current to the coil of the EMAT, thereby generating an ultrasonic wave that is reflected for multiple reflections by opposite surfaces of the object;

changing a frequency of the radio-frequency current, thereby finding a resonance frequency that make the object exhibit electromagnetic acoustic resonance by means of a detector connected to the coil of the EMAT; and determining the concentration of hydrogen contained in the object on the basis of an experimentally determined relation between a numerical value and the hydrogen concentration of the object, the numerical value being calculated by using an expression including the resonance frequency as a variable, wherein the numerical value is $f_n/f_m$, where $f_n$ is a resonance frequency of n-th order, and $f_m$ is a resonance frequency of m-th order.

5. The method according to claim 4 further comprising the step of measuring a thickness of an oxide film coating a surface of the object, wherein the relation used in the step of determining the concentration of hydrogen is experimentally determined for the thickness of the oxide film.

6. The method according to claim 4, wherein the object is a member of a nuclear reactor or a member of a fuel assembly charged in the nuclear reactor, said method further comprising the steps of:
 removing the object from the nuclear reactor;
 submerging the object in water filled in a pool annexed to the nuclear reactor;
 wherein the EMAT is disposed adjacent to the object and submerged in the water in the step of positioning the EMAT.

* * * * *